United States Patent
Fieback et al.

(10) Patent No.: US 6,615,906 B1
(45) Date of Patent: Sep. 9, 2003

(54) LATENT HEAT BODY

(75) Inventors: Klaus Fieback, Berlin (DE); Michael Matthäi, Henstedt-Ulzburg (DE); Toni Haberschuss, Bad Saarow (DE)

(73) Assignee: Schümann Sasol GmbH & Co. KG, Hamburg (DE)

( * ) Notice: Subject to any disclaimer, the term of this patent is extended or adjusted under 35 U.S.C. 154(b) by 0 days.

(21) Appl. No.: 09/540,453

(22) Filed: Mar. 31, 2000

(51) Int. Cl.$^7$ .............. F28D 17/00; B32B 3/26
(52) U.S. Cl. .................. 165/10; 428/304.4
(58) Field of Search .............. 165/10, 905; 428/304.4

(56) References Cited

U.S. PATENT DOCUMENTS

| | | | |
|---|---|---|---|
| 4,277,357 A | * 7/1981 | Boardman | 165/53 |
| 4,572,864 A | * 2/1986 | Benson et al. | 428/305.5 |
| 4,908,238 A | * 3/1990 | Vigo et al. | 427/389 |
| 4,931,333 A | 6/1990 | Henry | |
| 5,070,223 A | * 12/1991 | Colasante | 219/759 |
| 5,202,150 A | * 4/1993 | Benson et al. | 427/595 |
| 5,290,904 A | * 3/1994 | Colvin et al. | 428/68 |
| 5,305,821 A | 4/1994 | Weingartner | |
| 5,314,005 A | 5/1994 | Dobry | |
| 5,390,791 A | 2/1995 | Yeager | |
| 5,532,039 A | * 7/1996 | Payne et al. | 428/116 |
| 5,565,132 A | * 10/1996 | Salyer | 252/70 |
| 5,709,914 A | * 1/1998 | Hayes | 428/35.1 |
| 5,804,266 A | * 9/1998 | Salyer | 428/35.2 |
| 5,935,486 A | * 8/1999 | Bell et al. | 252/70 |
| 6,207,738 B1 | * 3/2001 | Zuckerman et al. | 524/156 |

FOREIGN PATENT DOCUMENTS

| | | |
|---|---|---|
| DE | 8408966 | 5/1984 |
| DE | 4307065 | 6/1994 |
| EP | 0165596 | 12/1985 |
| FR | 2536155 | 5/1984 |

OTHER PUBLICATIONS

Patent Abstracts of Japan vol. 097, No. 005, May 30, 1997 & JP 09 021592 A (Fuji Electric Co Ltd), Jan. 21, 1997.

* cited by examiner

*Primary Examiner*—Henry Bennett
*Assistant Examiner*—Tho V Duong
(74) *Attorney, Agent, or Firm*—Martin A. Farber

(57) ABSTRACT

Latent heat body (1) with paraffin-based latent heat storage material accommodated in a carrier material which has holding spaces, wherein the carrier material comprises fibres of an organic plastics material or natural material or of an inorganic material or of textile materials. The carrier material is assembled from individual carrier-material elements by adhesive bonding, capillary-like holding spaces for the latent heat storage material being formed at least between the carrier-material elements. The latent heat storage material is provided with a thickening agent for providing increased viscosity to the heat storage material while in a molten state.

3 Claims, 11 Drawing Sheets

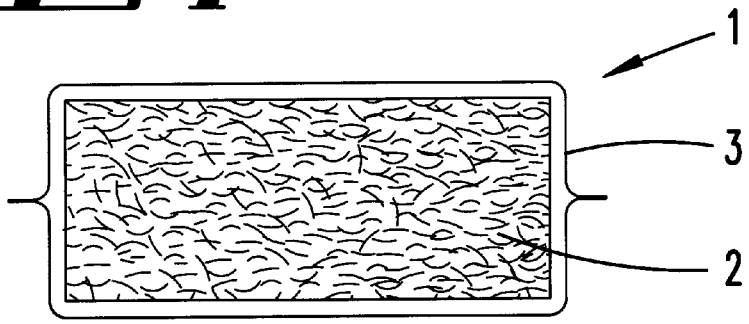
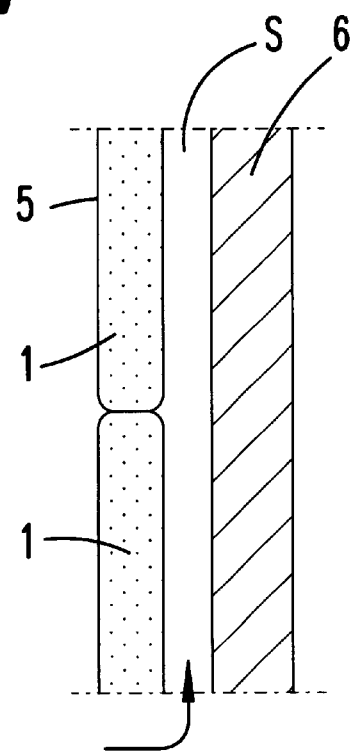
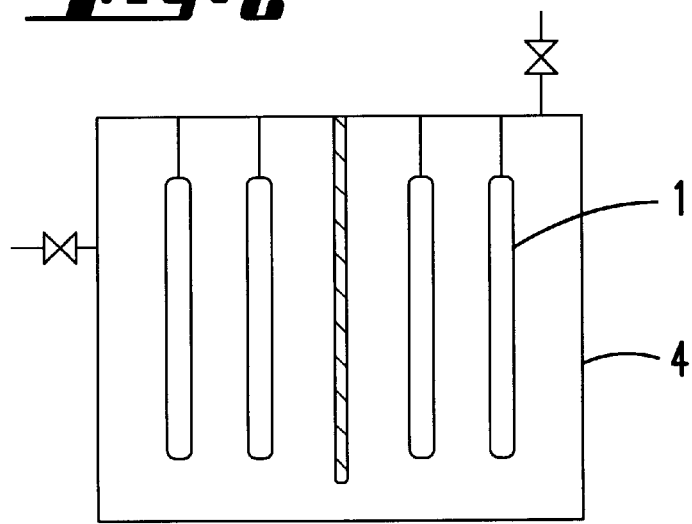

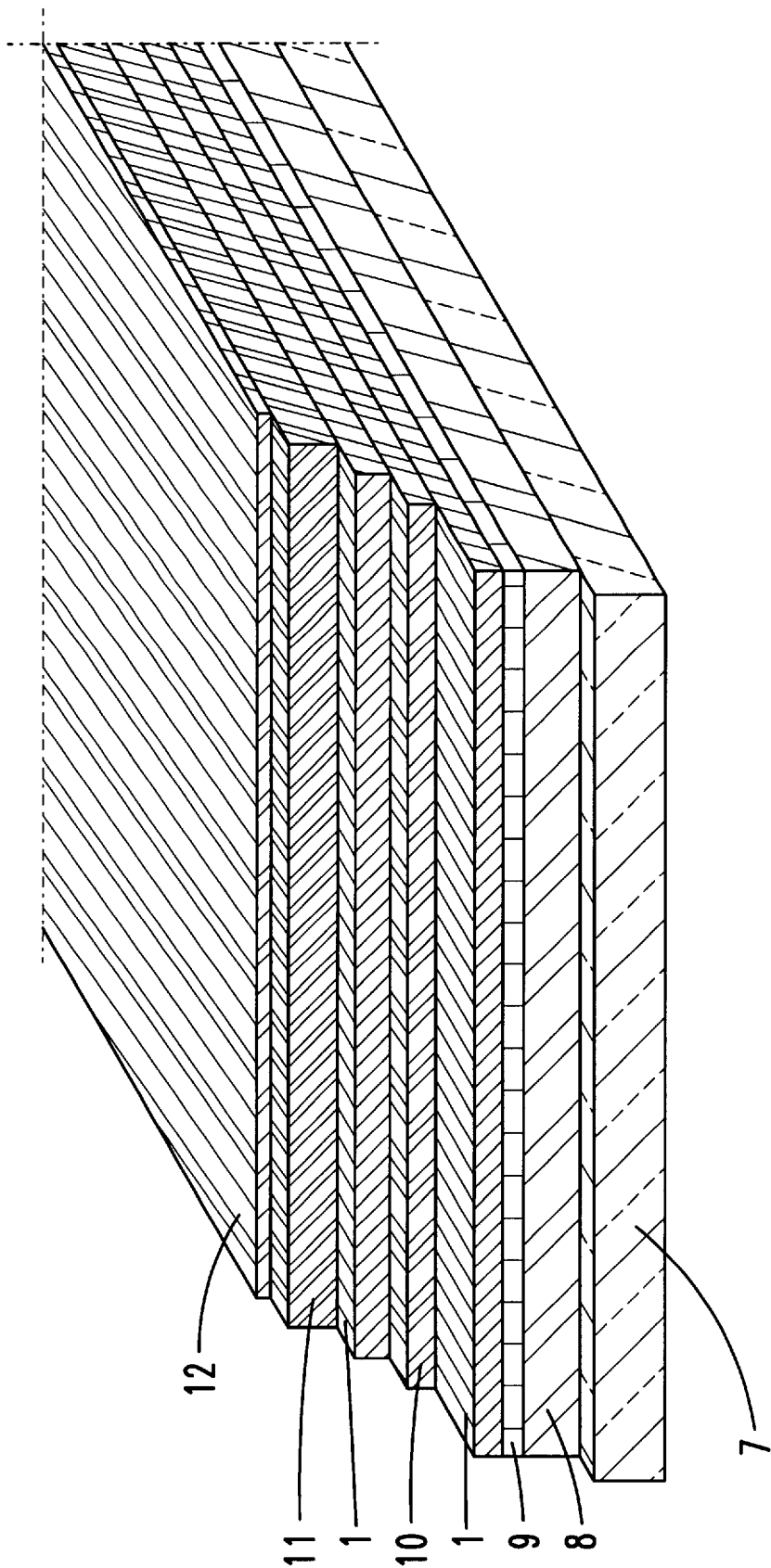

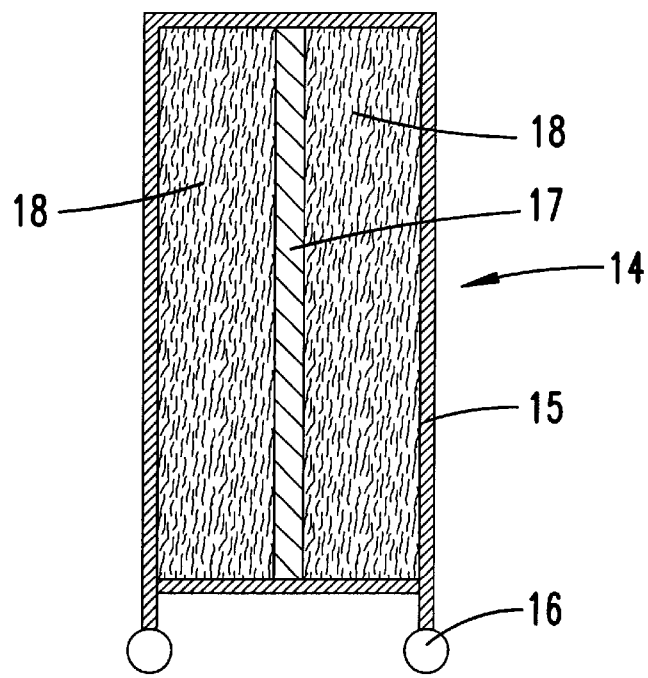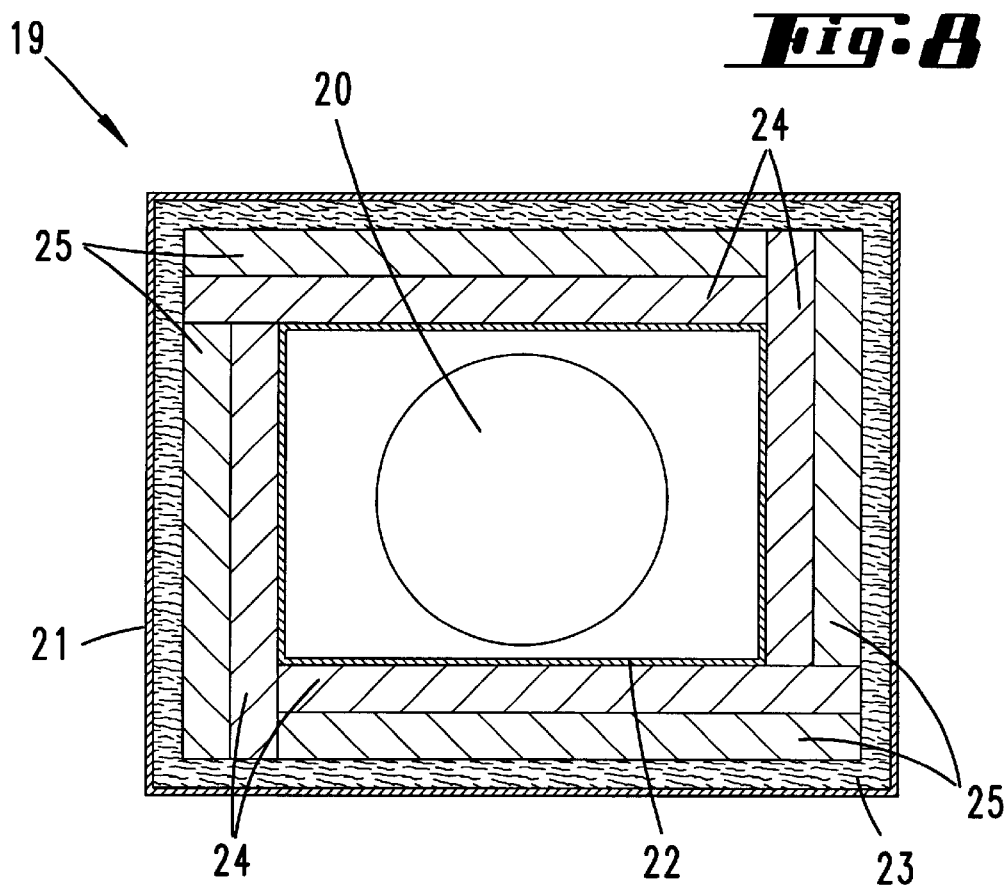

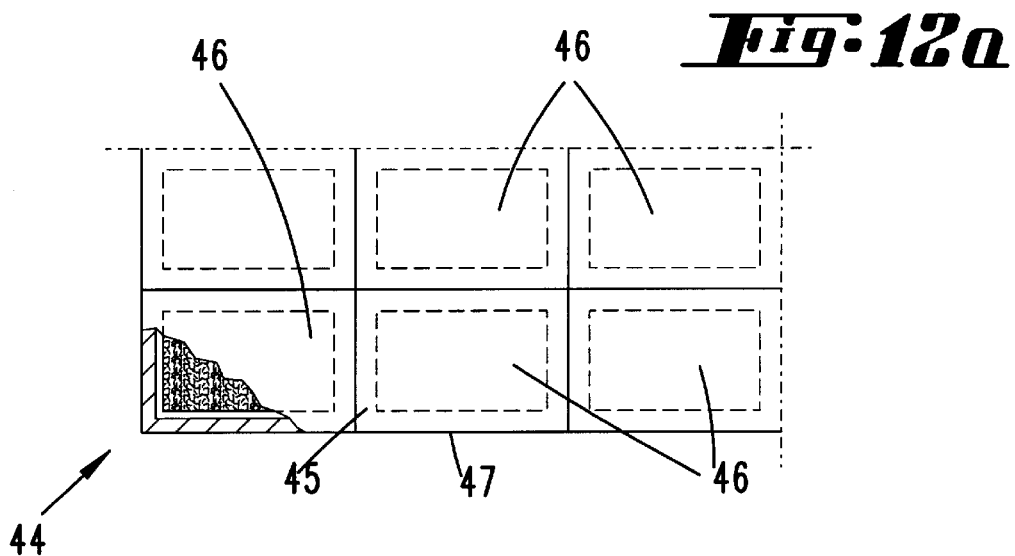
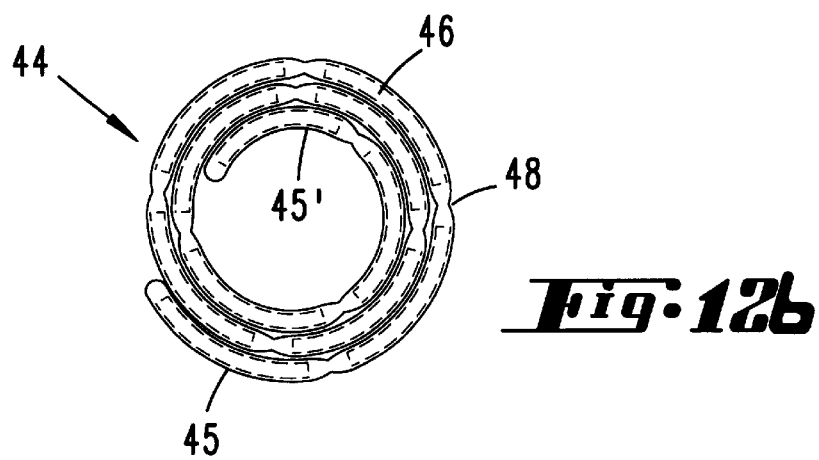
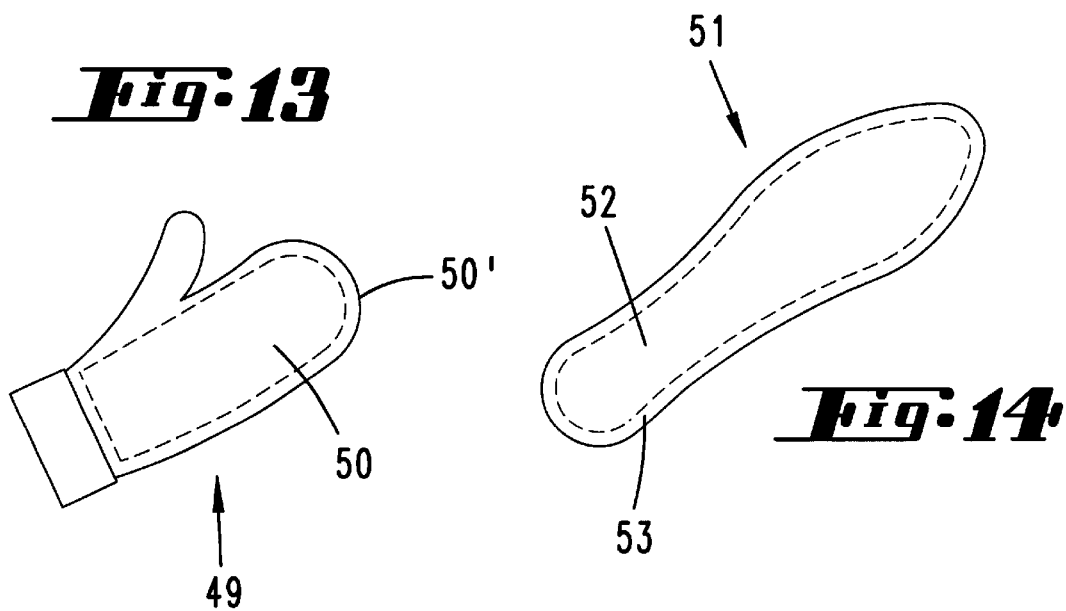

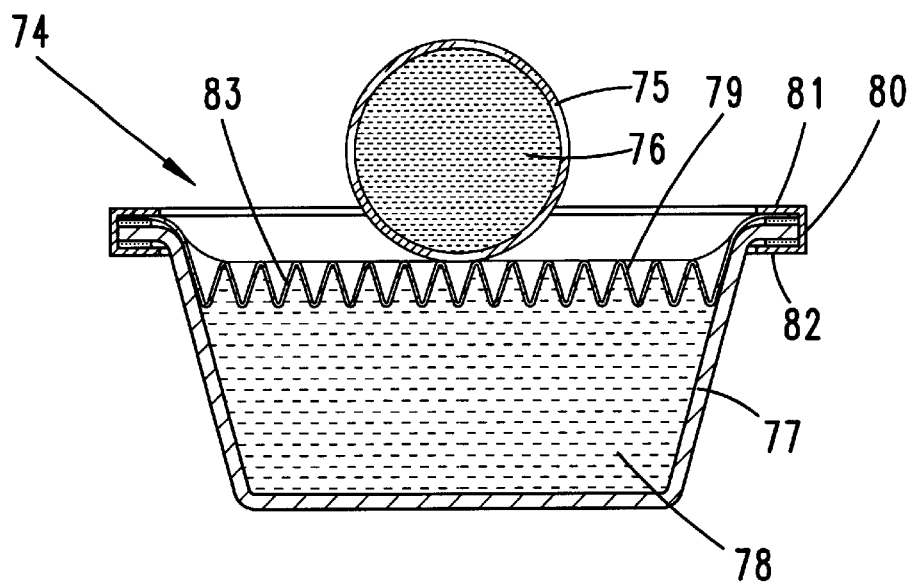
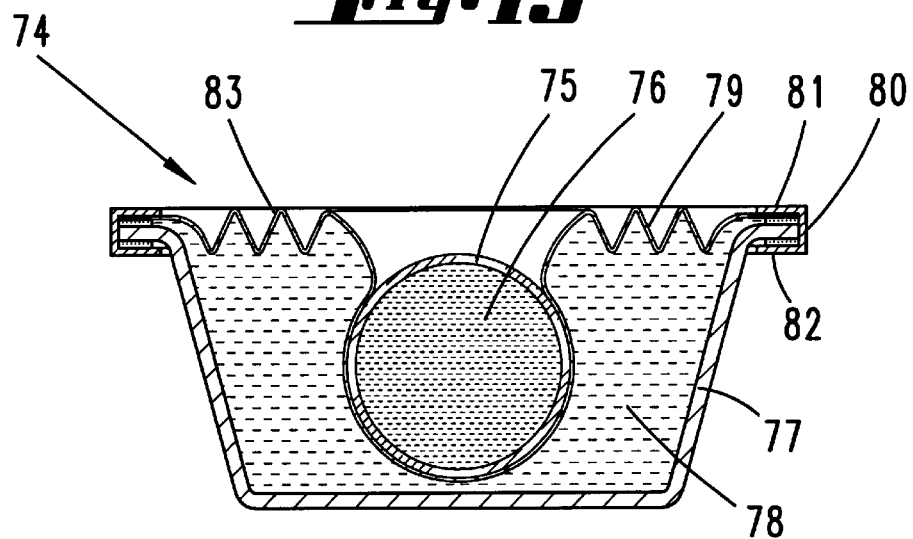
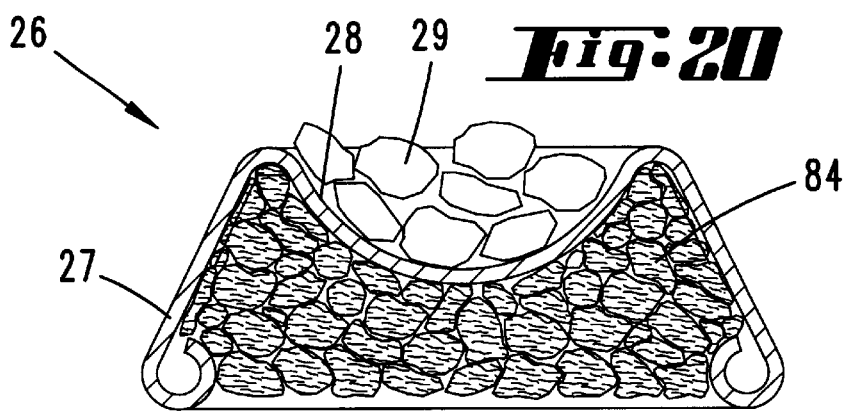

_US 6,615,906 B1_

LATENT HEAT BODY

FIELD AND BACKGROUND OF THE INVENTION

The invention relates to a latent heat body with paraffin-based latent heat storage material accommodated in a carrier material which has capillary-like holding spaces, the carrier material comprising an organic plastics material or natural material.

From German Utility Model 84 08 966, there is known a porous foam material as the carrier material. However, with this foam material it is impossible to achieve the structural strength desired even when the latent heat storage material is in the heated state. Moreover, the porous foam material cannot readily be impregnated with the latent heat storage material. Special measures, such as squeezing, have to be taken.

working on this basis, the invention deals with the technical problem of providing a latent heat body which, while being easy to produce, is highly efficient, i.e. has a high heat storage capacity and, at the same time, exhibits sufficient structural strength even in the heated state. It is also desired for the carrier material to be filled with or suck up the latent heat storage material automatically, as far as possible. It is also important to achieve a high retention capacity with regard to the latent heat storage material by means of the properties of the carrier material alone.

SUMMARY OF THE INVENTION

These technical problems are initially and substantially solved by assembling the carrier material from individual carrier-material elements which are inherently structurally strong or, when combined with the latent heat storage material, lead to the appropriate structural strength, for example by adhesive bonding. For the invention, it is important for the carrier-material elements to be held cohesively together even in the absence of latent heat storage material, and consequently the carrier material is one or more structures each comprising a multiplicity of combined carrier-material elements. According to the invention, the carrier-material elements are assembled in such a way that capillary holding spaces for the latent heat storage material are formed between them, which spaces may be in the form of a crack. The capillary holding spaces described above, due to their capillary action on a fluid, allow the carrier material to be filled with or to suck up the fluid in a substantially automatic manner and provide the carrier material with a high retention capacity. This action is used to good effect for the latent heat body according to the invention in that the proposed paraffin-based latent heat storage material to which individual additives, or a plurality of the additives, cited in this application may be added, is liquefied by heating to a sufficient extent for the automatic suction action to be observed. Preferably, the latent heat storage material can be heated up to a temperature which is above the highest melting point of the individual paraffins and additives contained therein. The latent heat storage material is in this way liquefied to such an extent that it can be taken up automatically by the carrier material until the latter is completely saturated. This procedure results in the advantage that it is possible to dispense with complex and therefore expensive technological process steps which involve a high input of in particular mechanical energy.

The assembly procedure which leads to a fixed bond between the carrier-material elements is at the same time suitable for setting the size of the holding spaces which remain between the carrier-material elements and for influencing the desired structural strength.

By virtue of the adjustability of the size of the holding spaces, there exists furthermore the possibility of establishing, as a function of the boundary or surface tension of the latent heat storage material, a size of the holding spaces which is optimized with regard to a maximum possible holding capacity and, at the same time, a sufficiently high capillary action.

Suitable carrier materials are organic materials such as plastics or cellulose. It is also preferable for a carrier-material element to have its own capillarity. An example is a cellulose fibre, such as a wood fibre, which inherently forms a considerably finer capillary space than the capillarity formed between two fibres. It is also important for the latent heat storage material itself to form homogeneously distributed hollow structures. These structures are of particular importance for the performance or response of the latent heat body. Firstly, such hollow structures provide yielding spaces as the volume changes during heating or cooling. This volume change may generally be of the order of 10% of the volume. As carrier-material elements, there may furthermore be used fibres of very different lengths and diameters. Suitable elements are in particular also ceramic fibres, mineral wool, plastics fibres and other suitable fibres, such as for example cotton or wool. Ceramic fibres used preferably substantially comprise $Al_2O_3$, $Si_2$, $ZrO_2$ and organic additions, and the quantities in which the components are present may vary considerably. Depending on the proportions selected, the density of the ceramic fibres fluctuates, preferably within a range from 150 to 400 kg/m³. With regard to the mineral wool, preference is given to using rock wool with or without the addition of thermosetting synthetic resins, and the wool may furthermore contain glass fibres. The density fluctuates as a function of the composition selected for the individual case and preferably lies in a range between 200 and 300 g/m³. Plastic fibres which are suitable as carrier-aterial elements preferably contain base materials such as polyester, polyamide, polyurethane, polyacrylonitrile or polyolefins. In this regard, it is particularly preferable for the latent heat storage material to be a paraffin as described in DE-A-43 07 065. The entire contents of this prior publication are hereby incorporated into the disclosure of this application, also for the purpose of including features of this prior publication in claims of the present application.

In the solidified state, such a paraffin has crystal structures which are modified by a structural additive, preferably so as to create hollow structures, such as for example hollow cones. This makes it possible to significantly improve the response of the latent heat storage material when heat is introduced. As a result, the latent heat storage material, such as paraffin, adopts, as it were, a porous structure. When heat is introduced, constituents of the latent heat storage material which melt more easily can flow through the hollow structures provided in the material itself. A type of microconvection is able to establish itself, if appropriate also with regard to air inclusions which are present. The result is a highly efficient mixing together. There is a further advantage with regard to the abovementioned expansion behaviour in the event of a phase change. The structural additive is preferably dissolved homogeneously in the latent heat storage material. In detail, structural additives such as those based on polyalkyl methacrylates (PA-MA) and polyalkyl acrylates (PAA) have proven suitable as individual components or in combination. Their crystal-modifying effect is brought about by the fact that the polymer molecules are incorporated into the growing paraffin crystals and prevent this crystal shape from growing further. Because of the presence of the polymer molecules even in associated form in the homogeneous solution in paraffin, paraffins may grow on the special supranuclear assemblies. Hollow cones which are no longer able to form networks are formed. Due to the synergistic action of this structural additive on the crystallization behaviour of the paraffins, cavities are formed and therefore the ease with which the heat storage medium paraffin can flow through (for example for air or water vapour which is included in the latent heat storage body or for liquefied phases of the latent heat storage material, i.e. of the paraffin itself) is improved compared to paraffins which have not been compounded in this way. In general, suitable structural additives also include ethylene/vinylacetate copolymers (EVA), ethylene/propylene copolymers (OCP), diene/styrene copolymers, both as individual components and in a mixture, as well as alkylated naphthalenes (Paraflow). The level in which the structural additives are present starts at a fraction of a per cent by weight, realistically at about 0.01 per cent by weight, and reveals significant changes, in terms of an improvement, in particular up to a level of about one per cent by weight.

In more detail, it is also preferable for an additive which leads to a thick liquid to be added to the latent heat storage material. A conventional thixotropic agent can be used for this. Even in the heated state, in which the latent heat storage material is usually liquefied, the consistency is then still that of a heavy liquid, in the sense of a gelatin-like consistency. Even in the event of such a latent heat storage body being cut into unintentionally, there is no leakage, or only insignificant leakage, of latent heat storage material.

Preferably, a latent heat body formed in this way is also completely surrounded with a cover, preferably a plastics film. The completely surrounding cover prevents any softened or liquefied latent heat storage material from leaking. The surrounding cover may also comprise urea. The sheet may be immersed in a molten covering material, i.e. for example urea or a plastic, such as for example nylon (polyamide). With urea, there is the advantage of a considerable flame-retardant action. It is particularly important to prevent leakage in the event of the rated operating parameters being exceeded. This applies in particular if the rated parameters are exceeded.

Preferably, the carrier structure comprises a fibrous body which is composed of individual fibres. In this case, commercially available fibreboards may be used, although relatively soft fibreboards are in this case preferred. Hard fibreboards are only able to accommodate the latent heat storage material to a limited extent. The fibres preferably have an inherent capillary action. When such a fibreboard is being impregnated with a paraffin-based latent heat storage material, the fibres fill up with paraffin by sucking it in and are "grown". In addition, the capillary spaces between the fibres are also filled with the latent heat storage material. A further configuration provides for the carrier material to be a nonwoven, for example a conventional absorbent nonwoven such as those which are commercially available for example for sucking up oil, acids or other liquids. In particular, it may be a nonwoven which consists entirely of polypropylene fibres. In this case, the fibres may also be joined together, for example by welding, in the sense of the general teaching mentioned above. However, the support structure provided by the nonwoven is also of independent importance. It is particularly advantageous that the abovementioned fibre mat, and also the nonwoven, are strengthened when impregnated with the paraffin-based latent heat storage material. The structure becomes more rigid. By way of example, a fibreboard of this nature acquires a higher compressive strength and is stronger when walked on, for example. In addition, the sound properties of latent heat bodies created in this way are also improved. There is a higher insulation against structure-borne sound. The footfall sound, for example when a latent heat body of this nature is used in the floor area, is effectively damped. In a further advantageous configuration, such carrier structures which can be impregnated with from two to ten times their own weight of latent heat storage material are used. By way of example, the abovementioned fibreboards are impregnated with from three to four times their own weight of latent heat storage material. However, the impregnation is not carried out to such an extent that over-swelling effects arise. It is also recommended to close off the capillaries on the outside, for example by grinding. This closure reinforces the effect of the surrounding cover mentioned above. In this case, it is advantageous for the capillaries to be closed off before the carrier material is impregnated with the latent heat storage material.

Further particular teaching of the invention relates to a configuration of the paraffin-based latent heat storage material which is such that there is still flexibility even in the strengthened state. Thus, in combination with the carrier-material elements, it is possible to achieve a flexible element, such as for example a seat cushion or a bandage. To this end, there is provision for the (paraffin-based) latent heat storage material to contain a proportion of mineral oil and/or of polymers, rubbers and/or elastomers. The rubbers and/or elastomers in particular lead to a higher flexibility. These are present in a proportion of less than 5%. If the polymers are not elastomers, they do not increase the flexibility and simply provide (possibly additional) protection against leakage the polymers amount to no more than 5% by mass of the latent heat storage material. Preference is given to a highly refined mineral oil, for example a mineral oil which is customarily referred to as white oil. The polymers are crosslinked polymers which are produced by copolymerization. Together with the mineral oil, by constituting a three-dimensional network or by their physical crosslinking (nodular structure), the crosslinked polymers form a gel-like structure. These gels exhibit a high level of flexibility combined with stability with respect to the action of mechanical forces. The paraffin is enclosed in this structure in the liquid state. When the phase changes, at crystallization, the paraffin crystals which are formed are surrounded by the gel structure, resulting in a mixture which overall is flexible.

In a possible application, a latent heat storage material which contains paraffin with a melting temperature of 50° C. and a copolymer with a melting temperature of 120° C., can be heated to a temperature of 125° C., so that initially the two components are mixed together uniformly, and the low-viscosity mixture can be absorbed by the carrier material, owing to the capillary forces which are active therein, until the carrier material is completely saturated. During subsequent cooling, the paraffin crystals which form are surrounded by the copolymer. At for example a possible upper operating temperature of the latent heat body of 80° C., only the paraffin component, but not the copolymer, is liquefied. This results in the advantageous effect that the paraffin cannot emerge from the copolymer, but rather remains in the carrier material with the copolymer. It is pertinent to the invention that the desired paraffin-retention capacity in the latent heat body when the carrier material described above is used can be achieved even where the copolymer forms less than 5% by mass of the latent heat storage material. The desired paraffin-retention capacity can be achieved even when the copolymer forms significantly less than 5% by mass in particular by means of an interaction carried out in a controlled manner of capillary forces in the holding spaces of the carrier material and/or of crystal structures of the paraffins which are influenced by means of structural additives and/or of the thixotropic agents which thicken the latent heat storage material and/or by means of the above-described closure of the capillaries and, if appropriate, a surrounding cover of the latent heat body. One advantage of the invention in this case is that as the content by mass of copolymers decreases, the content by mass of paraffins in the total mass of the latent heat storage material increases, and in this way it is possible to achieve a higher heat-absorption capacity while the total mass remains unaltered.

Together with the carrier material which is described in more detail above, a further result is a desired structural strength in the context of flexibility. However, other carrier materials than those mentioned above may also be employed. Examples include open-cell foams. With regard to the polymers, possible examples are styrene-butadiene-styrene (SBS), styrene-isoprene-styrene (SIS) or styrene-ethylene/butylene-styrene (S-EB-S). In the case of the styrene-ethylene/butylene block copolymer, use is made of an agent which is known under the trade name "KRATON G", marketed by Shell Chemicals. However, other known Kraton modifications may also be employed. This block copolymer is preferably suitable as a thickening agent for increasing the viscosity or as an agent for increasing the elasticity. The thickening agent may be a delayed action agent. Kraton G is a thermoplastic, and there are a number of types of copolymers in the Kraton G series which are of different structures. It is possible to differentiate in particular between the block and triblock copolymers, the molecular weight of which varies and which exhibit different ratios of styrene content to elastomer content. Of the known Kraton G types, the types known as G 1650, G 1651 and G 1654 may preferably be used.

Furthermore, it is also possible to use copolymers, such as for example HDPE (high-density polyethylene), pp (polypropylene) or HDPP (high-density polypropylene).

A further subject of the application is a paraffin-based latent heat storage material which contains an additive in one of the forms described above. Both the latent heat body and the latent heat storage material may furthermore and in combination contain an additive which forms the hollow structures mentioned above.

The paraffin-based latent heat storage material according to the invention may furthermore also be used without a carrier material, i.e. without a supporting matrix. For reasons of melting/storage capacity and for functional reasons, the copolymer content is always less than 5%. The gel formed is held in container sleeves, such as for example film/foil bags.

The pertinent factor is for the abovementioned additive of mineral oils and polymers on the one hand to be homogeneously distributed in the paraffin or for the paraffin to penetrate homogeneously through this additive and, on the other hand, for there to be no chemical interaction between the additive and the paraffin. Furthermore, it is particularly important for the selection to be made in such a way that there are virtually no differences in density between the additive and the paraffin, so that it is impossible for such density differences to cause any physical separation.

As has already been explained in the introduction, it is possible, in combination with one or more of the features explained above, for the latent heat body according to the invention to contain a number of latent heat part-bodies. In the context of the invention, a latent heat part-body is a cohesive, separate part or constituent of a latent heat body according to the invention which is inherently able to combine all the physical, chemical and structural features of the latent heat body or any desired selection of these features. Preferably, a latent heat part-body contains a carrier-material part and the latent heat storage material which is accommodated in capillary-like holding spaces in this carrier-material part. The abovementioned carrier-material part may have any desired combinations of the features of a carrier material which have been explained so far. In a preferred embodiment, the latent heat body contains a relatively large number, which is partly determined by its size and shape, of latent heat part-bodies, which can be arranged next to one another in regular and/or irregular form. In this way, it is possible to produce latent heat bodies of virtually any desired shape at low cost, since the latent heat part-bodies can be produced in large numbers on an industrial scale irrespective of the shape of the desired latent heat bodies. In a preferred configuration of a latent heat body formed from a plurality of latent heat part-bodies, the carrier-material parts which are included in the latent heat part-bodies also adjoin one another. These carrier-material parts are to be clearly distinguished from the carrier-material elements from which the carrier material, as explained above, is assembled, for example by adhesive bonding. Within individual carrier-material parts, the carrier-material elements form cohesive structures which include capillary-like holding spaces. However, adjacent latent heat part-bodies may also be held cohesively together if, for example, the arrangement is such that carrier-material elements of mutually adjoining carrier-material parts hook together in the respectively adjacent cohesive structures. Latent heat part-bodies may be held more cohesively together by connecting the latent heat storage material by means of adjacent latent heat part-bodies.

Preferably, the volumetric ratio of latent heat body to latent heat part-bodies has a value of at least 10, although lower or significantly higher volumetric ratios may also be appropriate. Moreover, an individual latent heat body may also contain latent heat part-bodies of different sizes and/or shapes. Furthermore, it is also possible for individual latent heat part-bodies to be of elongate shape and to be formed as strips, at least in the broadest possible sense. Alternatively, a latent heat part-body may also be in the form of a flake. Furthermore, the latent heat part-bodies may also be formed in the shape of spheres, ellipsoids, cubes, cuboids, pyramids, cylinders and the like. The selection of the number, sizes and shapes of the latent heat part-bodies of a latent heat body may in this case be oriented according to the size and shape of the desired latent heat body and to the particular requirements in terms of strength or deformability. In a further preferred embodiment of the latent heat part-body, the latter has a surrounding cover which comprises, for example, a film/foil material, in particular an aluminium foil or a polypropylene film. A film/foil offers the advantage of ease of deformability, so that adjacent latent heat part-bodies can nestle against one another, and it is substantially possible to avoid cavities between the latent heat part-bodies. As an alternative, or in combination with this measure, it is possible for a number of adjacent latent heat part-bodies also to be provided with a common outer surrounding cover, which may likewise be one of the films/foils mentioned above.

Furthermore, it is possible for the common outer surrounding cover to have a comparatively rigid wall, i.e. a wall which is more difficult to deform than the latent heat body or the latent heat part-bodies. If a rigid wall of this nature is formed as a hollow body, its interior space can be virtually completely filled with latent heat part-bodies of size, shape and number which are appropriate to the particular requirements, even if the common outer surrounding cover is of complicated geometric shape. In this case, a pressure may be applied to the latent heat part-bodies, in order to prevent relatively large cavities from forming in the rigid common surrounding cover, so that these part-bodies are compacted at least in certain areas. In the case of latent heat part-bodies of a latent heat body which have been compacted in this way, the cavities between latent heat part-bodies may, for example, form less than 1% by volume of the total volume of the latent heat body. The surrounding cover of the individual latent heat part-bodies and/or the common surrounding cover of the latent heat part-bodies of a latent heat body are in this case preferably configured in such a way that they are impermeable to latent heat storage material.

In an alternative advantageous configuration of a latent heat body, the latter contains a plurality of latent heat part-bodies which are surrounded by a common sleeve which is permeable to a heat transfer medium and which are preferably spaced apart from each other within this sleeve. By virtue of the spacing between the latent heat part-bodies, cavities are formed between the part-bodies, which cavities represent suitable flow paths for the heat-transfer medium. In particular, there is provision for a heat-transfer medium to pass out of an outer surrounding region, through the outer surrounding cover, which is permeable to this medium, of the latent heat body, into the interior of this body, where it flows through the cavities formed between the latent heat part-bodies and then leaves the latent heat body again through its common surrounding cover, which is permeable to this medium. A latent heat body which has heat-transfer medium flowing through its interior in this way is distinguished by a particularly rapid heat transfer from or to a heat-transfer medium. The common surrounding cover of the latent heat part-bodies may, for example, be in the form of a network or lattice, i.e. both readily deformable and rigid structures are possible. The entry and outlet openings in the common outer surrounding cover of the latent heat part-bodies contained in the latent heat body are suitably dimensioned in such a way that the heat-transfer medium can enter and leave the latent heat body substantially without obstruction and that moreover it is impossible for any latent heat part-bodies to pass through these openings. The volumetric ratio between the latent heat part-bodies contained in the surrounding cover and the cavities located between these part-bodies may lie within a wide range and, in numerical terms, may be considerably higher or lower than one. If a liquid is used as heat-transfer medium, the density of the latent heat part-bodies may be set in such a way that they are held suspended in the heat-transfer medium. In this way, the cavities formed are maintained, but it is possible to further accelerate the heat exchange with the latent heat part-bodies by causing them to circulate in flow terms. Examples of suitable liquid heat-transfer media are water or oils and, in addition, other suitable liquids. Even if a gaseous heat-transfer medium, e.g. air, is used, it is possible to counteract settling of the latent heat part-bodies which are contained in the common surrounding cover by effecting a controlled flow which leads to the latent heat part-bodies floating or circulating continuously. This can be enhanced by a particular configuration of the latent heat part-bodies, in which a surface area which is in each case large in relation to the weight of a particular latent heat part-body is effected. Consideration may be given, for example, to providing the latent heat part-bodies in the form of flakes. Furthermore, the latent heat part-bodies may have one or more of the features mentioned above.

As has already been stated, a latent heat body formed as above can be installed as a floor panel in a floor heating system.

However, the invention also relates to further applications of such latent heat bodies.

A first application comprises a plate heat exchanger which has such latent heat bodies as its plates. In this case, medium can be applied to the plate elements on both sides. By way of example, regenerative heat exchangers, such as those which are known in thermal power stations, may also be equipped with such heat exchangers. Specifically, such a plate element may also be of helical shape. To form and maintain the helical configuration, spacer elements are disposed between the layers, although this also applies to plate elements with planar surfaces. These spacer elements are arranged in the form of a grid, in such a manner that flow paths are left open.

In a further embodiment, it is preferred for such a plate element to be formed as a cladding panel in the construction sector. In this case, it is particularly advantageous if the cladding panel is disposed at a distance from the wall of a house. The chimney effect which is then established between the house wall and the cladding panel, which in this case is formed as a latent heat storage element, can thus bring about a cooling effect, partially by storing heat in the latent heat body. Furthermore, the thermal behaviour over the course of time is also improved. For example, after the sun has set, the latent heat body still continues to emit heat, including radiant heat, at constant temperature to the wall of the house over a prolonged period. At the same time, such a latent heat body constitutes a panel which provides a relatively high heat insulation. The insensitivity of such a cladding panel to the effects of weathering is also advantageous. The impregnation with paraffin also provides a hydrophobic property.

In further detail, a capillary-breaking grid structure, for example made from a plastics, may also be arranged in such a latent heat body, in addition to the carrier structure described above, for all the applications which have been described in the preceding text. In this way, the necessary equilibrium between capillary forces and gravity, when the latent heat body is arranged in a vertical position, can be achieved at any time in the filled fibrous structure. To allow the diffusion of water vapour, suitable overflow openings, such as slots, holes and the like, are located in the latent heat bodies. It is particularly important here for the thermal conductivity of this grid structure to approximately correspond to that of the latent heat storage material. Conventional metal structures are therefore to be rejected, since the thermal conductivity is too high.

With regard to the embodiment of a floor heating system comprising latent heat bodies of this nature, it is also proposed for latent heat bodies containing different latent heat storage materials in terms of the melting temperature or the phase-transition temperature to be arranged above one another. In this case, the latent heat body on which a heater element, such as for example a resistance-heating wire, acts directly is suitably equipped with latent heat storage material of the highest phase transition temperature, while the latent heat storage body with the phase-transition temperature which is lowest in relative terms is arranged close to the surface of the floor. Such a floor heating system can advantageously be provided as a night storage heating system, since the time offset can be used to good effect without, as with other known night storage heating systems, having to accept excessive temperatures.

The invention furthermore relates to a process for producing a latent heat body with paraffin-based latent heat storage material accommodated in a carrier material which has holding spaces. According to the invention, it is specified that the latent heat storage material is liquefied, and that the latent heat storage material which has previously been liquefied is fed to capillary-like holding spaces in the carrier material which suck the liquefied material in automatically. Liquefaction of the latent heat storage material may in this case preferably be achieved by heating. The liquefaction aims to make the latent heat storage material able to flow readily, i.e. essentially at achieving a low viscosity and a homogeneous state without the inclusion of relatively large pieces of solid material. The low viscosity provides an essential condition for the latent heat storage material to penetrate into the holding spaces, under the automatic sucking action of the capillary-like holding spaces in the carrier material, when it is fed to these spaces. To this end, the carrier material may, for example, be impregnated with liquefied latent heat storage material. The liquefied latent heat storage material may, for example, be fed to automatically sucking capillary-like holding spaces in the carrier material by immersing the carrier material in liquefied latent heat storage material. Before and/or during this immersion, process parameters which influence the automatic uptake of the latent heat storage material in the carrier material can be influenced so as to promote this uptake. By way of example, thermal energy may be continuously supplied to the latent heat storage material in order to promote the liquefaction. Furthermore, pressure may be applied to the liquefied latent heat storage material, thus likewise promoting the automatic uptake of the latent heat storage material in the capillary-like holding spaces in the carrier material.

The automatic sucking action of the holding spaces of the carrier material for liquids is based on the capillary-like form of the holding spaces which has already been mentioned above. The automatic sucking action of the capillary-like holding spaces for liquefied latent heat storage material and its attempt to retain this material are intensified as the size of diameter of the capillaries or of the inner radii of capillaries is selected to be smaller and as the surface tension of the latent heat storage material with respect to air is selected or set to be higher, and as the extent to which the carrier material selected can be wetted by latent heat storage material increases. In the process according to the invention for producing a latent heat body, on the basis of these relationships for setting a desired, in particular a maximum possible automatic sucking action of the holding spaces with regard to the latent heat storage material, it is possible to proceed in such a way that a carrier material with a surface tension which is as high as possible is selected and in such a way that the individual carrier-material elements have inner capillaries with preferably low radii of curvature and/or external shapes with narrow radii of curvature, in particular also have sharp edges or corners. Preferably, the carrier material is assembled from individual carrier-material elements, for example by adhesive bonding, and capillary-like holding spaces are formed at least between the carrier-material elements. When assembling the carrier-material elements it is therefore also possible to influence the automatic sucking action, in that preferably narrow, in particular crack-like capillaries are formed in order to increase this action. Furthermore, the process according to the invention may be employed to produce a latent heat body based on carrier material and latent heat storage material having all the features described above or having combinations of selected features.

In a suitable variant of the process according to the invention, the carrier material which has been impregnated with latent heat storage material is divided into a number of latent heat part-bodies, in which case the division may be carried out by means of sawing and/or cutting and/or tearing or also according to further known separating methods. For example, it is possible to impregnate a fibreboard made from cellulose fibres, which has been selected as the carrier material, with paraffin-based latent heat storage material which has previously been liquefied and to saw the impregnated carrier material into elongate, in particular strip-like latent heat part-bodies. As a further variant, a fibrous nonwoven, for example, which has been selected as the carrier material, after impregnation with latent heat storage material, could be torn into a desired number of comparatively small latent heat part-bodies, in which case the latter may be of flake-like form or of some other form. In one refinement of the production process according to the invention, the latent heat body and/or the latent heat part-bodies may be compressed, in order in this way to be compacted or given a preferred shape. It is also possible for the latent heat body and/or the latent heat part-bodies to be provided with a surrounding cover which may comprise a film/foil, in particular an aluminium foil or a polypropylene film. In this case, it is preferable for the latent heat body or the latent heat part-bodies to be completely surrounded by a surrounding cover which is impermeable to latent heat storage material and to be sealed in this cover, for example by welding, in such a manner that it is impossible for any latent heat storage material to leak out of the surrounding cover. In a refinement of the process according to the invention, the latent heat part-bodies of the latent heat body may also be provided with a surrounding cover which surrounds them together and may likewise have the properties mentioned above. In particular, it is possible to provide a readily deformable common surrounding cover which, in combination with a multiplicity of relatively small latent heat part-bodies contained therein, leads to a desired deformability of the latent heat body. As an alternative, it is possible to use a common surrounding cover which has a higher rigidity or lower deformability than impregnated carrier material. A surrounding cover of this nature, which may be any of a large number of types of casing used in everyday items, may, according to a variant of the process according to the invention, be filled with any desired number of latent heat part-bodies, and then, in a further working step, the latent heat part-bodies can be sealed in the common surrounding cover. It is thus possible, using the process according to the invention, to virtually completely fill any desired cavities in everyday items with impregnated carrier material in a simple, time-saving and inexpensive manner.

In an advantageous refinement of a latent heat body according to the invention, there is provision, in conjunction with one or more of the features which have been explained thus far, for at least one microwave-active substance to be present in the latent heat body. A microwave-active substance in the context of the invention is to be understood as meaning a substance which is internally heated under the influence of radiation from so-called microwaves owing to its molecules being excited to move by the high-energy electromagnetic radiation. Microwaves are adjacent to the wavelength range of infrared radiation, at higher wavelengths. In this respect, a minimum wavelength of approximately $1.4 \times 10^{-3}$ m is to be assumed, and the internal heating can be optimized within the wavelength range which is of technical interest by adapting the wavelength selected to the molecular structure of the microwave-active substance which is to be used. A latent heat body which contains a microwave-active substance of this nature consequently has the advantage that considerably shorter times are required to supply a certain amount of energy compared to heat transfer through shorter-wave radiation, thus allowing correspondingly quicker heating. In particular, consideration is given to distributing the microwave-active substance uniformly in the latent heat body, so that a corresponding uniform heating is to be observed. In the context of the invention, uniform distribution does not necessarily have to mean an homogeneous distribution, since uniform heating of the latent heat body as a result of thermal conduction processes which is adequate for technical applications may also be achieved when the microwave-active substance is distributed along the latent heat body in accumulated patches which are sufficiently close together. In this connection it is possible, for example, for carrier-material elements to contain the microwave-active substance, for the microwave-active substance to be contained in capillary-like holding spaces between the carrier-material elements, which for example have been assembled to form a carrier material by adhesive bonding, or in capillary-like holding spaces inside the carrier elements, or for the microwave-active substance to be contained in cavities which are formed between a plurality of latent heat part-bodies; combinations of these proposed distributions are also conceivable. A uniform distribution of the microwave-active substance in the latent heat body is promoted by the microwave-active substance being contained in it in powder and/or granule and/or fibre form. If the microwave-active substance is to be held in the latent-heat-body cavities which are formed between latent heat part-bodies, finally relatively large cohesive structures of the microwave-active substance may also be advantageous, with dimensions which may be of comparable size to those of the latent heat body. Consideration may be given in particular to an interwoven mesh or network of a microwave-active substance which is integrated into the latent heat body. As an alternative, or in combination with above-described forms of distribution of the microwave-active substance as a solid body, it may be expedient for the microwave-active substance to be a liquid at least at the temperature at which the latent heat body is used, in which case, in this context, all flowing media are to be included in this definition. In terms of selecting the microwave-active substance, in principle all substances which experience internal heating under the action of microwaves are to be considered for the purposes of the invention. It is preferably a substance which is included in one of the materials groups consisting of glass materials, plastics materials, minerals, metals, in particular aluminium, coal and ceramics. It is also possible for a plurality of different microwave-active substances to be combined with one another in a latent heat body. This allows more rapid heat transfer to the latent heat body at a plurality of wavelengths or within a definable wavelength range. Preferred embodiments of the microwave-active substance which may be mentioned by way of example are granular glass bodies, granular plastics, mineral fibres, ceramic fibres, coal dust, metal, in particular aluminium powder, and a filament/wire, which is likewise preferably formed from metal and may be processed further to form an interwoven mesh.

To produce a latent heat body which can be heated by microwaves, a microwave-active substance has to be added to the latent heat body or a constituent of this body in a process step which preferably aims to achieve a uniform distribution of the microwave-active substance in the latent heat body. The procedure may be such that the microwave-active substance is added to the carrier-material elements while they are being produced. In particular, the carrier-material elements may also themselves be produced directly from microwave-active substance. As an alternative, or in combination with this measure, it is possible to incorporate the microwave-active substance continuously or discontinuously in the capillary-like holding spaces which are formed when the carrier material is being assembled from carrier-material elements, for example by adhesive bonding, while this assembly is taking place. This may, for example, be achieved by the fact that, with a layered structure of the carrier material, after a respective layer has been completed by adhesive bonding of carrier-material elements, a microwave-active substance which is in dust or powder form is dusted onto the surface of the layer and, after excess dust or powder has been removed, a further layer of carrier-material elements is placed on top, these process steps being repeated as many times as desired. In a latent heat body which contains a plurality of latent heat part-bodies, the microwave-active substance may furthermore also be incorporated in the cavities which are formed between latent heat part-bodies. The microwave-active substance may in this case be processed both as a powder and as granules or fibres and, furthermore, also as a larger structure, in particular as a filament/wire or an interwoven mesh. In this case, the procedure is preferably such that, firstly, a layer of latent heat part-bodies is arranged, for example, in a common surrounding cover, and then the microwave-active substance is deposited on this layer and in the spaces between these part-bodies, and then a further layer of latent heat part-bodies is applied; it is possible to repeat these working steps as many times as desired. In a further variant to the production process according to the invention, the microwave-active substance is added to the latent heat storage material before the latent heat storage material is fed to the capillary-like holding spaces in the carrier material. In this case, it should preferably be ensured that the microwave-active substance is distributed uniformly in the latent heat storage material, so that the microwave-active substance is also sucked into the capillary-like holding spaces in the carrier material in a uniform distribution, where it is present in a uniform distribution with the paraffin-based latent heat storage material. As an alternative, or in combination with the processing of the microwave-active substance in the solid state described above, it is also possible for the microwave-active substance to be added to the latent heat body in liquid form; in this case, in principle all the addition techniques described above are to be considered.

If the microwave-active substance in its crude state cannot be used directly in the production of a latent heat body, the process according to the invention for producing a latent heat body which is to be heated by microwaves comprises additional process steps in which a desired state of the microwave-active substance can be achieved. These steps include, for example, working the microwave-active substance into a powder, granules or fibres, preferably by mechanical processes such as for example sawing, cutting, milling and tearing. If it is intended to use the microwave-active substance in filament/wire form or as an interwoven mesh, the process according to the invention for producing a latent heat body which can be heated by microwaves also encompasses process steps in order to process the microwave-active substance into structures which are appropriate for the particular requirements. In particular, these steps include the wire-drawing of suitable materials and further processing of the wires obtained to form an interwoven mesh.

BRIEF DESCRIPTION OF THE DRAWING

In the following text, the invention is explained in more detail with reference to the appended drawing which, however, merely illustrates exemplary embodiments. In the drawing:

FIG. 1 shows a cross section through a latent heat body which is based on a fibreboard;

FIG. 2 shows a latent heat store with latent heat storage bodies arranged therein;

FIG. 3 shows a cladding panel containing latent heat storage bodies;

FIG. 4 shows a structure relating to a floor heating system;

FIG. 7 shows a vertical section through a mobile storage heater with latent heat bodies;

FIG. 8 shows a horizontal section through a transport container for medical purposes, containing latent heat bodies;

FIG. 11a shows a plan view of a storage element for air/water heat exchangers with latent heat bodies welded in;

FIG. 12a shows a plan view of a heating/cooling blanket with welded latent heat bodies sewn in;

FIG. 12b shows a side view of the heating/cooling blanket as shown in FIG. 12a, in a rolled-up arrangement;

FIG. 13 shows a glove with latent heat bodies welded integrally therein;

FIG. 14 shows a sole of a shoe, in the form of latent heat bodies welded in as a film/foil;

FIG. 18 shows a sectional view of a drinks cooler with latent heat storage material at the beginning of the cooling operation;

FIG. 19 shows a drinks cooler in accordance with FIG. 18, with an embedded drink container, during the cooling operation;

FIG. 20 shows a vertical section through a dog food container with a latent heat body which contains a multiplicity of latent heat part-bodies.

DETAILED DESCRIPTION OF THE PREFERRED EMBODIMENT

Figure 5:
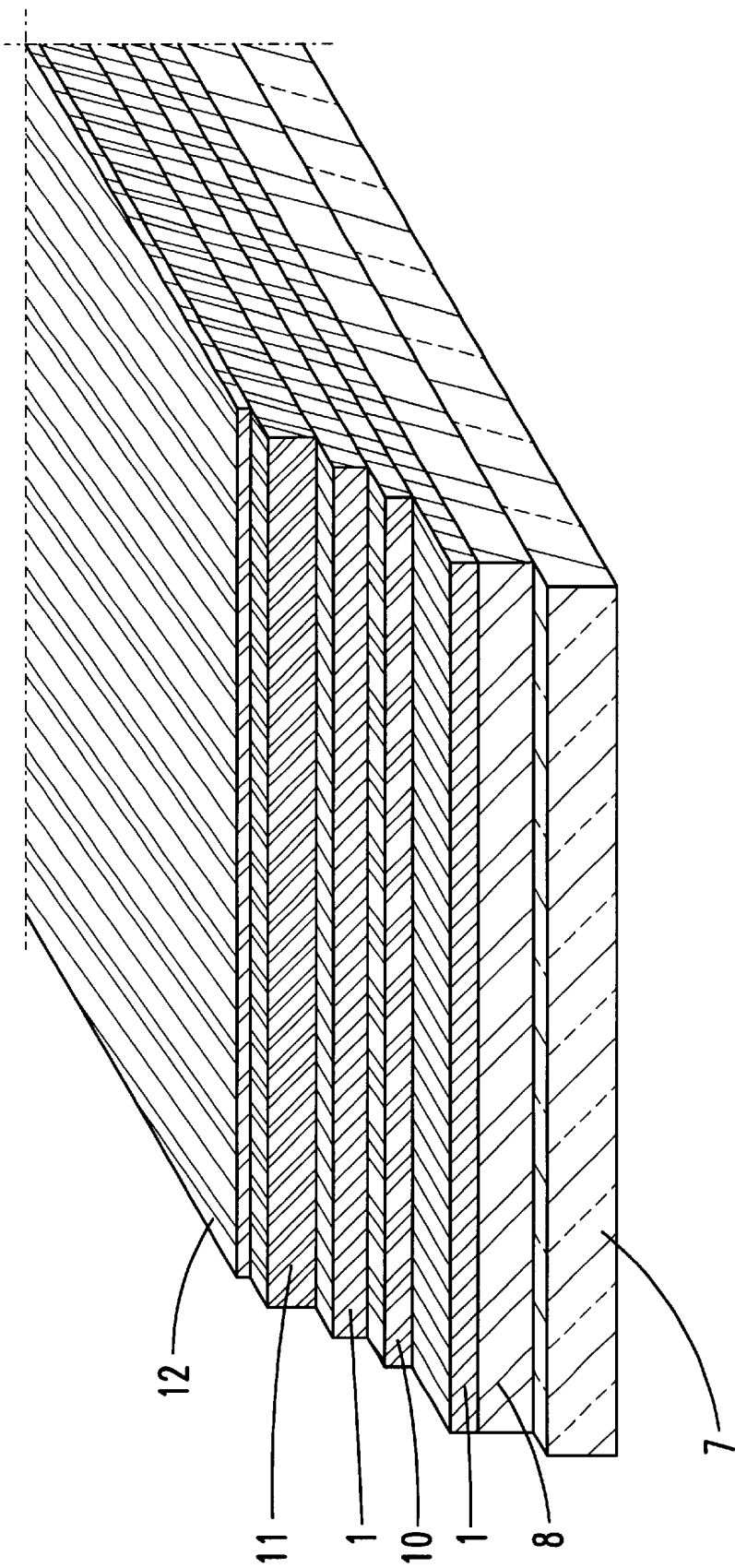
FIG. 5 shows an alternative embodiment of a structure in accordance with FIG. 4.

Initially with reference to FIG. 1, the invention describes and illustrates a latent heat body 1 which comprises a fibreboard 2 which is impregnated with a paraffin latent heat storage material, and a surrounding cover 3. The fibreboard 2 is a soft fibreboard which is filled with a paraffin latent heat storage material. The filling is effected in the form of an impregnation.

Specifically, FIG. 1 shows a fibreboard made from poplar wood fibres which is comparatively soft in the unimpregnated state. However, it is also possible to use other cellulose fibres. In the unimpregnated state, the fibreboard has a density of approx. 200 kg/m$^3$. Preference is given to fibreboards which have a density in the range from 150–300 kg/m$^3$ in the unimpregnated state. In the impregnated state, the density of the fibreboard is approx. 700 kg/m$^3$. Preference is given in this state to a range from approx. 50–800 kg/m$^3$. The paraffin represents approximately 50% by volume of the structural matrix, while the paraffin or the latent heat storage material forms approx. 68% by mass of the matrix.

The fibreboard may also be provided with a flame-retardant additive. It is surprising that there are virtually no perceptible changes in dimension of the fibreboard in terms of whether the latent heat storage material is in the solid or liquefied state. This is particularly so if the latent heat storage material is provided with an additive which, as stated in detail above, leads to the formation of inherently hollow structures. Such a fibreboard may also be used as an air heat transfer plate or a water heat transfer plate and as a wall storage panel.

As an alternative, an impregnated fibrous sheet based on a nonwoven is also proposed, although not specifically illustrated in the drawing. It is preferable to use a highly porous nonwoven, for example polypropylene fibres. In the unimpregnated state, such a nonwoven may have a density of approx. 100 kg/m$^3$, with a preferred range of approx. 70–150 kg/m$^3$. When impregnated with paraffin, such a nonwoven-based sheet has a weight of approx. 700 kg/m$^3$, in a range from approx. 600–800 kg/m$^3$. In this case, the volume of latent heat storage material in the matrix is approx. 65%, while by mass it represents approx. 85%. Such a fibrous sheet may also be of transparent or opaque design. The essential factor is that such a sheet should be flexible even in the solidified state of the latent heat storage material. In addition to the particular applications mentioned above, it may also, for example, be used as a mat, for example for greenhouses.

As an alternative to one of the fibreboards described, it is also possible, if appropriate in combination with a fibreboard, to use a nonwoven or a textile as the impregnated body. Textiles of significance are in particular woven or knitted cotton fabrics.

The surrounding cover 3 comprises an aluminium foil. However, it may also be a polypropylene film.

In FIG. 2, a first possible application is shown. There is a latent heat store 4 in which a plurality of latent heat bodies 1 are arranged suspended in a vertical position. Air, for example, may flow through the latent heat store 4. However, in the same way, water can also flow through the latent heat store. In the process, the heat is then stored in a manner known per se in the latent heat bodies 1 and can subsequently be released again when a relatively cooler heat transfer medium flows through.

In the exemplary embodiment shown in FIG. 3, the latent heat bodies 1 are formed as cladding panels. Special structures may also be formed on the outer side 5. By way of example, slate slabs or the like may be prefitted on this side. In addition to the arrangement as a cladding panel, the other essential factor is that a gap S should remain between a masonry wall 6 and the latent heat bodies 1. The gap S may, for example, if it has a bottom and top opening, be used to provide a chimney effect. In this way, the climatic conditions, and in particular adaptation to the day-night cycle, can be improved significantly. The result is a phase-shifted cooling or heating effect. Since the latent heat storage material is initially only heated up to the phase transition temperature, and then a certain holding effect takes place, it takes longer for the heat to "break through". Conversely, when the heating from the sun is no longer present, the excess heating is rapidly dissipated, but on the other hand a prolonged warming effect at approximately the same level remains when the phase-transition temperature is reached.

In FIG. 4, 7 denotes the concrete floor in a building, this floor being provided between stories. An insulating layer 8, comprising for example a polyurethane foam, is provided as thermal insulation on the concrete floor 7. In the case of an air heating system, air ducts 9 which can be used to introduce hot air through hot air are formed above the insulating layer 8. Furthermore, a first layer of a latent heat body 1 in one of the configurations as described herein is arranged above the air ducts 9. Above these air ducts, there is a further heating arrangement 10 which may, for example, comprise water pipes or an electric heating system. Above this, a further layer is formed by a latent heat body 1 in one of the configurations described here. Finally, above this, there is a layer of dry floor pavement 11, and at the top the structure is sealed by means of a floor covering 12, for example a carpet or tiles.

The design of the floor structure shown in FIG. 5 corresponds to that shown in FIG. 4, except in this case there are no air ducts 9. The first layer of latent heat bodies 1 is arranged directly against the thermal insulation 8. This is followed by the heating arrangement 10 and, above this, the second layer of latent heat bodies 1.

Figure 6:
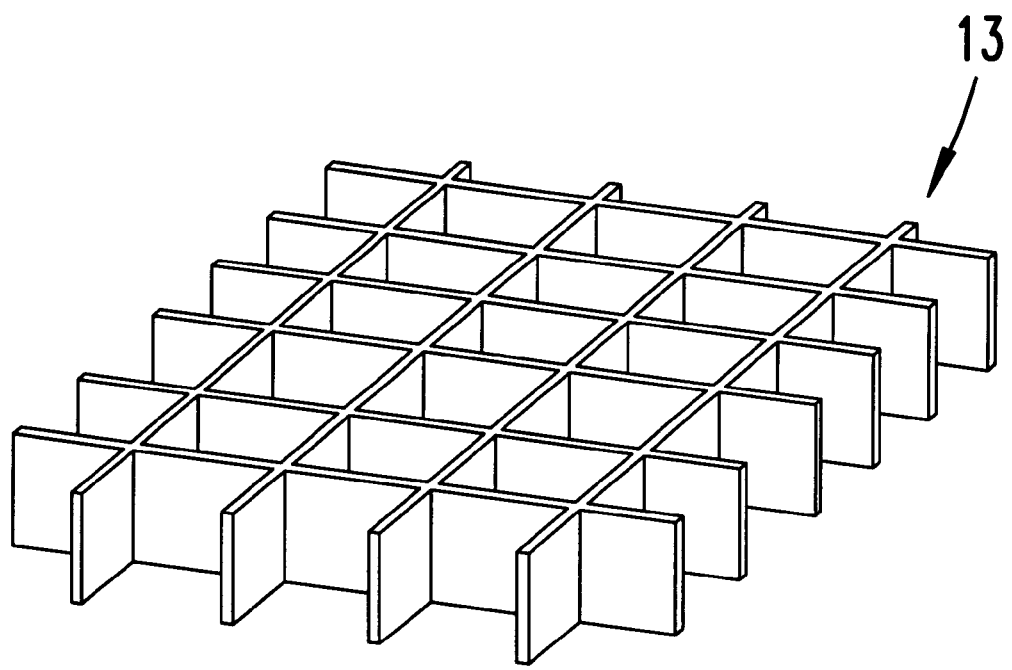
FIG. 6 shows a diagrammatic view of a supporting structure for incorporation in a fibreboard.

In FIG. 6, a supporting structure 13 is shown which is formed as a pattern of compartments or a grid structure. The supporting structure 13 is preferably made from a plastics material and has a similar thermal conductivity to that of the latent heat storage material.

FIG. 7 shows a mobile storage heater 14 which has an outer casing 15 and can be moved on rollers 16. Inside the casing, there is a heater element 17 which may be formed, for example, from wires through which current flows, and latent heat bodies 18 are arranged on both sides of this heater element. When the heater element 17 is switched on, the heat which it dissipates is preferably absorbed by the storage elements 18, which are arranged with their surfaces parallel to the heater element, and is dissipated to the environment uniformly through the casing 15 for a prolonged period even after the heater element 17 has been switched off.

In FIG. 8, there is shown a horizontal section through a transport container 19 for medical purposes, for example for storing or transporting stored blood products or organs 20. The container comprises a stable outer casing 21 and an inner container 22 which is held at a spacing therefrom so that it has space to turn, this inner container having smaller dimensions than those of the outer container. The inner side of the outer container is continuously lined with an insulating layer 23 which may be conventional insulating bodies, for example Styropor. The remaining space between the insulating layer 23 and the inner container 22 is used to hold latent heat bodies 24, 25 which, in the example shown, are impregnated wooden fibre elements. In this case too, however, it is possible to use latent heat bodies which have been produced from an impregnated nonwoven fabric or further such bodies which are described in the application. In the exemplary embodiment shown, latent heat bodies 24, are arranged in pairs with parallel surfaces, so that the space between the inner container 22 and the insulating layer 23 is completely filled by these bodies. In this case, a plurality of pairs of latent heat bodies 24, 25 are arranged offset with respect to one another. Other arrangements which appear expedient are also possible as an alternative to the arrangement illustrated. The latent heat bodies 24 and 25 may differ in terms of the phase-transition temperatures of their respective latent heat storage materials, so that an optimum storage action can be set as a function of the ambient temperature of the outer container 21 and the desired temperature in the inner container 22, by means of a multi-stage store with selected phase-transition temperatures. The transport container 19 furthermore has a base (not shown) and a lid which is pivotably attached, for example by means of hinges, a composite structure of an insulating layer 23 and latent heat bodies 24, 25 advantageously also being provided in the base and lid area.

Figure 9:
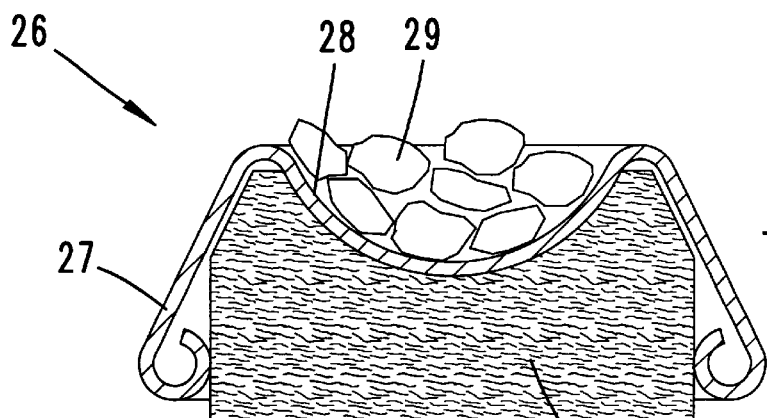
FIG. 9 shows a vertical section through a dog food container containing latent heat bodies.

FIG. 9 shows a vertical section through a dog food container 26 which has an outer casing 27, on the top side of which a recess 28 for the dog food 29 is provided. The inner chamber of the feed container, which lies both beneath and to the sides of the recess, is used to hold a latent heat body 30 which, in the preferred application, serves as a cooling element and exchanges heat with the dog food via the wall area of the recess 28, which is formed with a good thermal conductivity.

Figure 10:
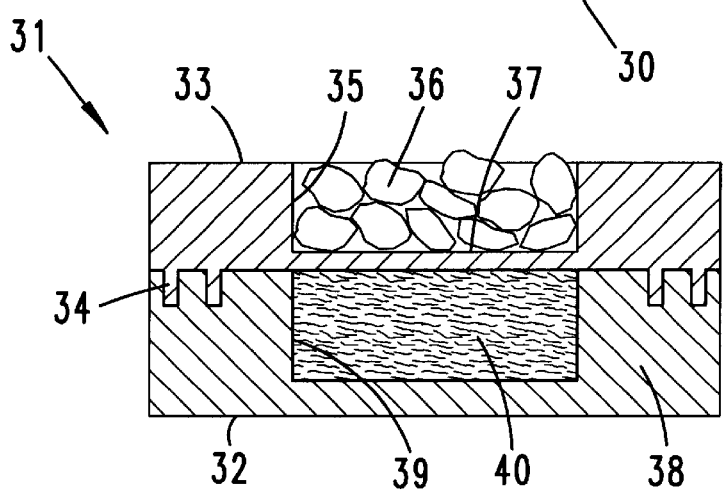
FIG. 10 shows a vertical section through a cat food container containing latent heat bodies.

The cat food container 31 which is illustrated in vertical section in FIG. 10 comprises a lower casing 32, on which an upper casing 33 is positioned and has been centred by means of a centring device 34. The centring device 34 may comprise pin-like or bead-like projections in the upper part 33 and recesses of matching shape and position in the lower part 34, but may also be provided in some other advantageous way. The upper part 33 has a recess 35 for holding the cat food 36, the base area 37 of the recess 35 preferably being thin-walled and made from a material with a good thermal conductivity. In its interior, the lower casing 32 has a thermal insulation 38 which, for its part, is provided on its top side with a chamber 39 for holding a latent heat body 40. In this context, all the embodiments which have been described in the application are suitable latent heat bodies 40. According to the illustration, there is provision for the underside of the upper casing 33, when it has been placed on the lower casing 32, to be in contact with the latent heat bodies 40 in the region of the chamber 35, with their surfaces parallel, resulting in good heat transfer between the animal feed and the latent heat body. The feed containers described with reference to FIG. 9, 10 may also be used to hold other types of animal feed, which are not specifically mentioned.

Figure 11A:
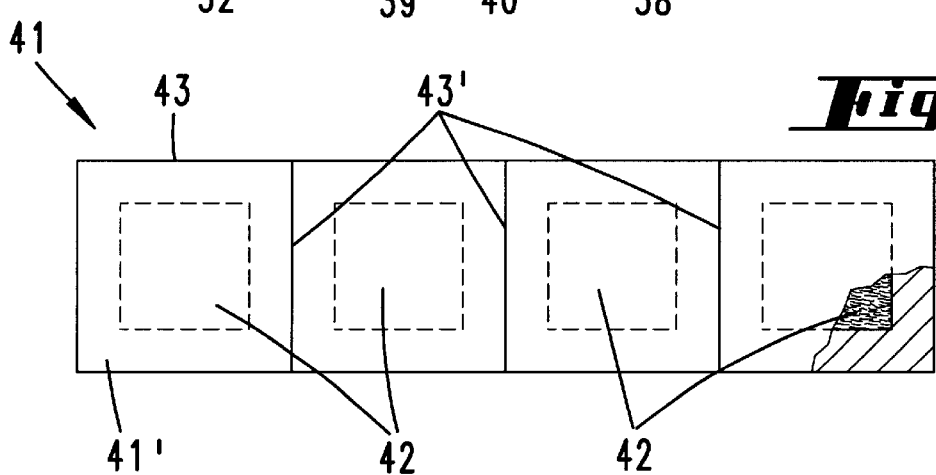

FIG. 11a shows a plan view of a storage element for air/water heat exchangers 41 which, in this example, is formed from four latent heat bodies 42 which are welded into a weld-in sheet 41'. As an alternative to the arrangement of four latent heat bodies 41 in a row which is illustrated, it is also possible for any other number and arrangement of latent heat bodies to be realized in a storage element of this nature. All the embodiments of latent heat bodies which are described in the application can be used for the application shown. In the exemplary embodiment illustrated, there is provision for the latent heat bodies 42 to be arranged between two pieces of sheet 41' which are placed together and are joined by weld seams 43, 43' all the way around. Furthermore, it is proposed for the weld seams 43' between adjacent latent heat bodies 41 to be formed as preferred bending or breaking areas, so that the storage element 41 can be given different forms for use in different applications without the latent heat bodies 42 being damaged.

Figure 11B:
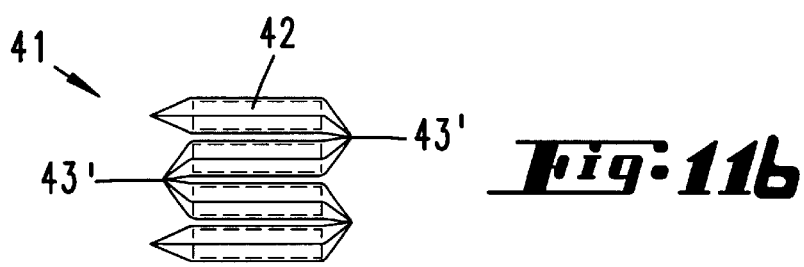
FIG. 11b hows a side view of the storage element shown in FIG. 11a in a folded-up arrangement.

FIG. 11b shows a side view of the storage element for air/water heat exchangers in accordance with FIG. 11a in a possible folded-up arrangement.

FIG. 12a shows a plan view of a heating/cooling blanket 44 in the extended position. As emerges in connection with FIG. 12a, which shows a rolled-up state of the blanket 44 in side view, the blanket 44 comprises two fabric layers 45, 45' which are arranged parallel to one another and between which a number of individual latent heat bodies 46, which are welded into protective sleeves (not shown in more detail), are sewn in.

In accordance with the exemplary embodiment shown in FIG. 12a, 12b, the fabric layers 45, 45' are joined together between the latent heat bodies 46 by means of peripheral seams 47 and intermediate seams 48, so that they are held together internally without the risk of latent heat bodies 46 slipping. The heating/cooling blanket 44 illustrated can be used, for example, as a baby blanket or an accident blanket. Therefore, flexible latent heat bodies 46 in which the carrier material may be a nonwoven are preferably used in this application. While FIG. 12a shows a plan view of only part of an open heating/cooling blanket 44, FIG. 12b shows a side view of a rolled-up arrangement of a complete blanket. As an alternative to the exemplary embodiment illustrated, designs with a different shape, number and arrangement of latent heat bodies 46 are also conceivable.

FIG. 13 shows a plan view of a further possible application in a glove 49, which has latent heat bodies 50, 50' sewn in between its inner and outer fabric layers, which are not illustrated in more detail. In this application, it is again preferable to use flexible latent heat bodies in which the carrier material may be a nonwoven.

FIG. 14 shows an insole 51 for a shoe. According to this figure, it is proposed to weld a latent heat body 52, which preferably exhibits flexible properties, into a film/foil 53; further sole layers (not shown) may be attached to the top and/or bottom of the sole 52. In this case, structured layers made from materials such as for example foam or rubber may preferably be used on the underside of the sole in order to prevent the insole 51 from slipping in the shoe. Textile layers, for example including padded fabric layers, may preferably be used on the top side of the sole 51 in order to additionally increase the comfort of the wearer.

Figure 15:
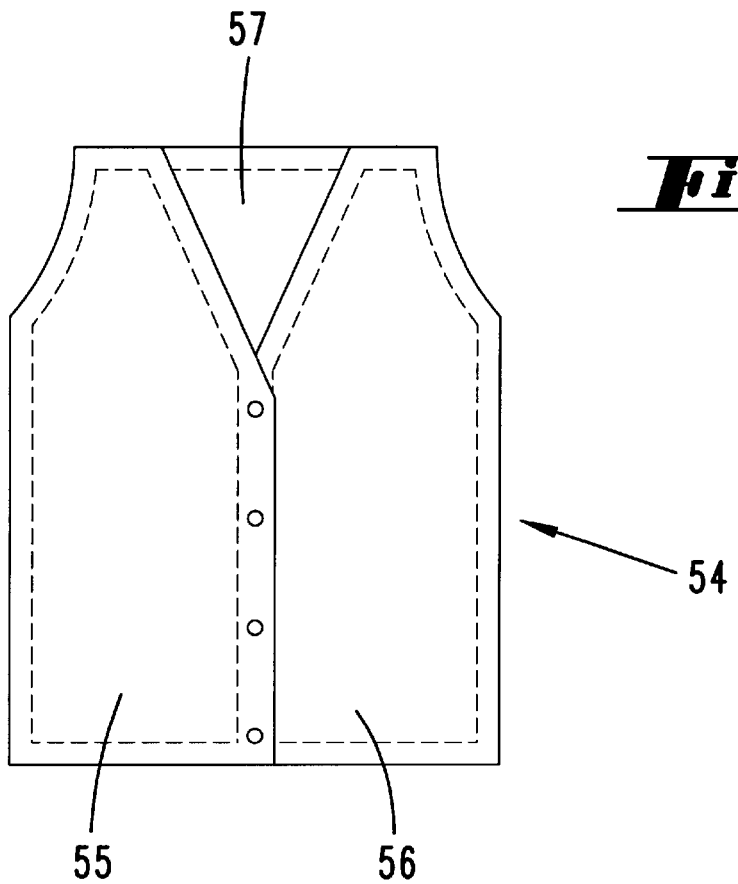
FIG. 15 shows a waistcoat with latent heat bodies which are welded in integrally in a film/foil.

FIG. 15 shows a plan view of a waistcoat 54, between the various inner and outer material layers of which (not shown in more detail) latent heat bodies 55, 56 and 57 are sewn. In order to make the waistcoat as comfortable as possible to wear, it is in this case preferable to use flexible latent heat bodies which are welded individually into a surrounding cover. Suitable surrounding covers are, for example, films/foils and, in particular, aluminium foil or polypropylene film.

Figure 16A:
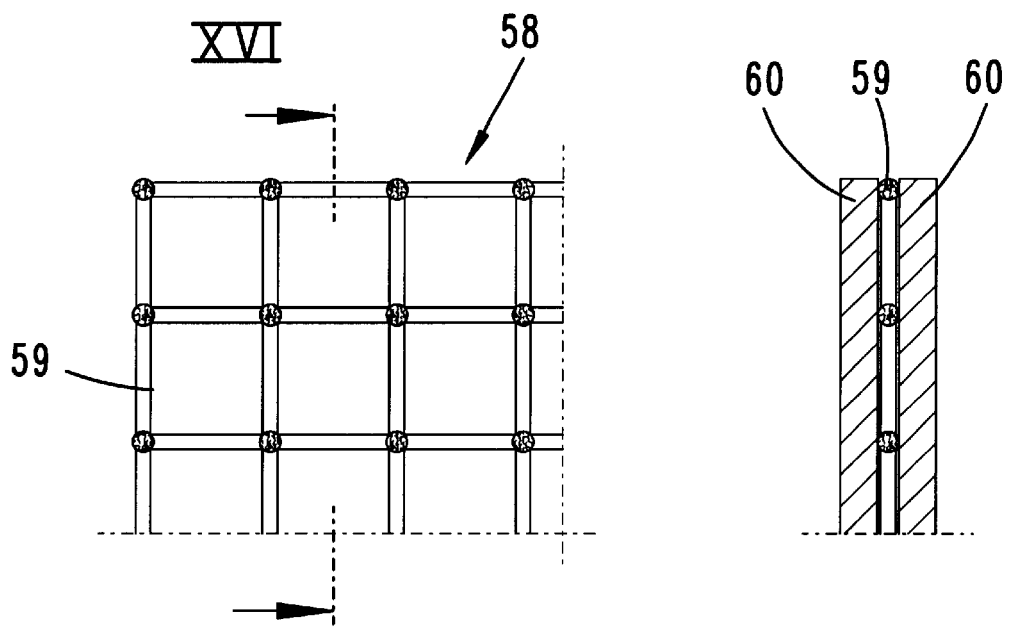
FIG. 16a shows a plan view of a latent heat body as a storage element for building constructions, in a design as impregnated grid structure.

FIG. 16a shows a view of a latent heat body 58 according to the invention which is provided as a storage element for buildings. According to this figure, the latent heat body has a grid-like structure of a carrier material 59 which may comprise textile materials, flax or other suitable materials with capillary holding spaces for the latent heat storage material according to the invention. According to the exemplary embodiment shown, the carrier material 59 is impregnated with latent heat storage material (not shown in more detail), the impregnated grid structure being permeable to water vapour and therefore allowing water vapour to diffuse in walls of buildings.

Figure 16B:
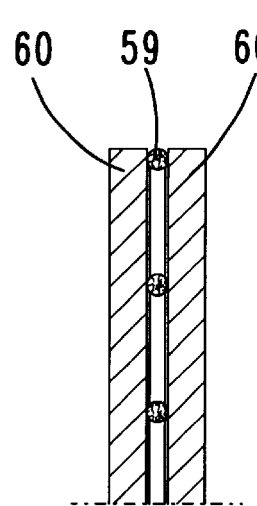
FIG. 16b shows a side view of the storage element according to FIG. 16a, in an arrangement between two wall panels.

FIG. 16b shows a preferred application of a storage element in accordance with FIG. 16a, shown in section on line XVI—XVI. According to this figure, the storage element 58 is arranged vertically, with parallel surfaces, between two wall panels 60, 60' which are spaced apart. As an alternative to the embodiment illustrated, other forms of grid structures are also possible.

Figure 17:
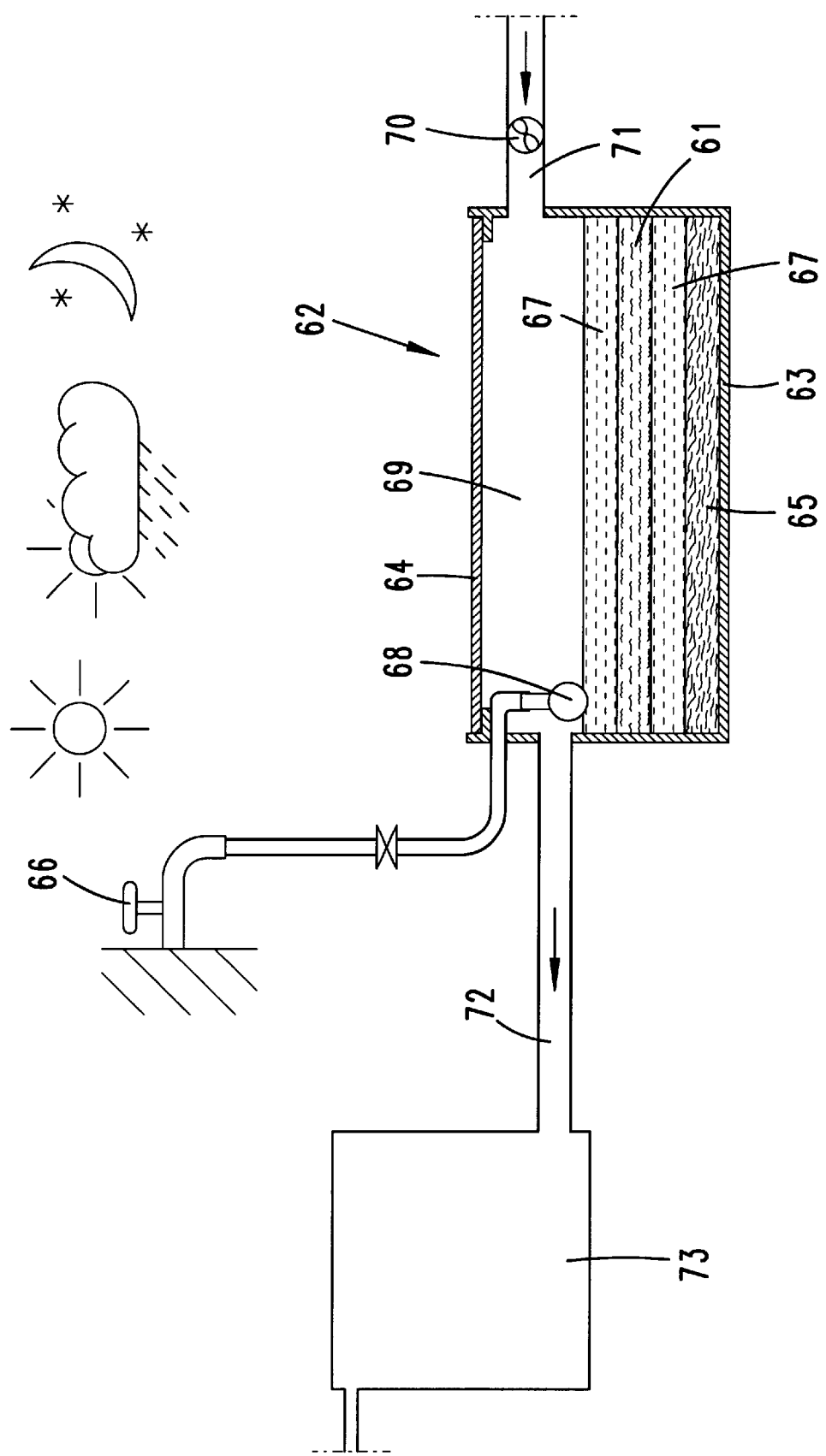
FIG. 17 shows a solar evaporator with latent heat body for a composter.

FIG. 17 uses a diagrammatic sketch to describe a preferred application of a latent heat body 61 according to the invention as a storage element for a solar evaporator 62. According to this figure, the solar evaporator has an outer casing 63 which, on the top side, is closed off by means of a cover 64, for example a glass panel, which allows high-energy radiation, for example solar radiation, to pass through. In the bottom region of the outer container, there is an insulating layer 65 which may be made from conventional insulating materials, for example Styropor. It is also possible for the side walls of the outer casing to be provided with corresponding insulating layers. Via an inlet 66, water 67 (for preference) is introduced into the casing; a desired filling level is not exceeded as a result of a safety valve 68 being used, which may, as illustrated, be a ballcock stop. In the space 69 which remains between the cover 64 and the water surface, air is preferably blown in by a fan 70 via a feedline 71, and this air is enriched with water vapour above the water level and, due to the excess pressure which builds up, escapes through a line 72 into a consumer 73, which in the application illustrated is a composter. The energy required to evaporate the water is fed to the container by means of high-energy radiation which is incident through the cover 64. The latent heat body 61 illustrated is located below the water surface and, in the exemplary embodiment shown, is attached, in a manner not shown in more detail, to side walls of the casing 63 using conventional attachment means. As an alternative, it is also possible for the latent heat body 61 to float unsecured in the water. For this purpose, it is proposed, if necessary, for means which push it upwards or downwards to be attached to the latent heat body, by which means the latent heat body is kept suspended in the surrounding water, so that it cannot rise to the surface or fall to the bottom of the container and all surfaces of the latent heat body participate in the heat exchange. Means for pushing the latent heat body downwards may be any desired weights, while means for pushing it upwards could, for example, be air-filled chambers. Compared to conventional solar evaporators, the advantage of the arrangement illustrated in FIG. 17 consists in the fact that the latent heat body 61 used, when subjected to intensive solar irradiation and therefore a high introduction of heat, takes up for storage much of the heat which is not required for evaporation and releases this heat to the surrounding water during cloudy weather and at night, when the incident radiation intensity is lower, so that the evaporation power becomes more even. For the application described in FIG. 17, the latent heat body 61 may be made from any of the carrier materials and latent heat storage materials which have been listed in the application. Owing to the negligible miscibility of the latent heat storage material with water, the latent heat body may moreover be used with or without a surrounding cover. If an outer surrounding cover for the latent heat body is dispensed with, the capillaries of the carrier material on the outer surface may be closed off by grinding or the like, resulting in additional protection against latent heat storage material leaking out into the environment.

The invention furthermore relates to cushions, mats, rolls, bandages, strips, belts and inlays, packaging, compresses for hot and/or cold application for medical, orthopaedic and veterinary purposes which are equipped with the latent heat body according to the invention. In this context, consideration is preferably given to the use of flexible latent heat bodies, for whose carrier material in particular a nonwoven, a fibrous sheet based on nonwoven or a flexible fibreboard produced from some other material are therefore particularly well suited. Further preferred applications of the latent heat body according to the invention relate to belts, inlays for hot and/or cold application for health purposes and in particular for use in sport, at leisure and/or at the workplace.

In addition to the transport container for medical purposes shown in FIG. 8, consideration may furthermore be given to employing latent heat bodies according to the invention, with or without surrounding containers and films/foils, for purposes of insulation and/or heat storage in further thermal transport and/or packaging means. Thermal containers for foodstuffs for commercial and/or domestic use also constitute a possible application area for latent heat bodies according to the invention.

In addition to the possible applications for construction purposes which have already been described in the application, there are further possibilities for use in the construction sector, for example to line swimming pools—in this case in particular unheated open-air pools—in order to make the water temperature, which is partially determined by solar irradiation, more even over the course of the day. In the construction sector, latent heat bodies according to the invention can be used not only to store heat but also as cold storage material. In this case, consideration may be given, for example, to applications in cold stores in which the latent heat bodies may be arranged, for example, behind wall lining panels, but also in the floor and/or ceiling area, and allow the room temperature to be reduced uniformly even if a refrigerating unit operates discontinuously. In this way, the switching frequency of the compressor is advantageously lowered.

Furthermore, latent heat bodies according to the invention may also be used in land, airborne and water-borne vehicles as latent heat and/or cold storage material. In this case, consideration is given, for example, to use in cargo compartments of delivery lorries, aircraft and ships. In this case, consideration is given, for example, to use in cargo compartments of delivery lorries, aircraft and ships, for example in container storage spaces.

The paraffin-based latent heat storage material which, in the applications described so far, is accommodated in capillary-like holding spaces in a carrier material may also in many cases be used without a carrier material. In this case, the heat storage material retains its heat storage function and, furthermore, is distinguished by easy, virtually unlimited deformability. A possible example of such an application is described with reference to FIG. 18, which shows a drinks cooler 74, by means of which it is possible to accelerate cooling of a drink 76 which is enclosed in a drink container 75 compared to the cooling achieved in known cooling devices. According to the exemplary embodiment shown, the drinks cooler 74 contains a container part 77, in the interior of which latent heat storage material 78 is contained. That surface of the latent heat storage material 78 which is not surrounded by the container part 77 is covered by a film/foil 79 which is connected to the edge of the container part 77 in such a manner that the latent heat storage material 78 cannot escape from the drinks cooler 74 even in the liquefied state. The film/foil 79 may be attached to the edge of the container part 77 using suitable attachment elements 80. In FIG. 18, a profiled section which engages around the edge of the container part 77, extends along the entire length of the edge and is connected to the film/foil 79 and the edge of the container part 77 by means, for example, of continuous adhesive layers 81, 82 or in some other connecting and sealing manner, is selected as an attachment element of this nature. As an alternative to the attachment element 80 which is selected to be a profiled section and, in addition to a sealing action, also fulfils a visual function, it is also possible to provide a direct seal between the film/foil 79 and the edge of the container part 77. Preferably, the dimensions of the film/foil 79 in the taut state exceed the distance between the edges of the container part 77, so that the film/foil 79, in its starting position, extends in wavy or corrugated form or even so that it overlaps itself in a more or less irregular manner over the surface of the latent heat storage material. By way of example, the sectional view of FIG. 18 shows an arrangement of the film/foil 79 with lamellae 83. To prepare for use, the drinks cooler 74 is placed in a cooling appliance, for example a refrigerator or a chest freezer, and is left there until the latent heat storage material has undergone a desired cooling. After it has been removed from the cooling appliance, a drink container 75, for example a beer bottle, is placed or stood on the outer surface of the film/foil 79, as likewise illustrated in FIG. 18. If the drinks cooler is oriented substantially horizontally, the drink container, due to its weight and the ready deformability of the film/foil and the latent heat storage material, sinks into the interior of the container part 77, coming into increasing contact with the film/foil which adjoins the latent heat storage material and being surrounded by this film/foil, resulting, as shown in FIG. 19, in the film/foil becoming increasingly taut in the plane of the container opening.

In FIG. 19, an arrangement has been reached in which the drink container 75 is virtually completely surrounded by the film/foil bearing against it and the adjoining latent heat storage material. Consequently, most of the outer surface of the drink container 75 is in direct heat-exchanging contact, via the film/foil 79, with the cooled latent heat storage material 78. The resultant very good thermal conduction from the drink container to the latent heat storage material which thus becomes possible provides very rapid cooling of the drink container and the drink contained therein. After desired cooling of the drink container or drink has been achieved, the drink container is removed from the drinks cooler. Then, depending on the deformability of the film/foil 79 and the materials properties, in particular the surface tension and viscosity, of the latent heat storage material 78, the latent heat storage material is restored to its original shape over time.

The above-described drinks cooler 74 may also be used to cool further objects, for example including solid foodstuffs. By reversing its principle of operation, it is also conceivable firstly for heating of the latent heat storage material to be effected in a heating appliance, for example in an oven, and, when it has been removed from the heating appliance, for this material to be employed to heat objects, for example containers holding solid or liquid foodstuffs. Furthermore, it is possible, instead of a film/foil 79 which is dimensioned with a larger surface area than the container opening, as shown in FIG. 18, 19, to use a film/foil which even in the load-free state is substantially taut and which, by dint of its ready elasticity, allows a body which is to be cooled or heated to sink into the interior of the container due to the load imposed by the weight of this body.

Even when the paraffin-based latent heat storage material is used without a carrier material, it is possible for the latent heat storage material to contain one or more of the additives described above in order to achieve advantageous properties. In this case, it is preferable to use additives which impart gel-like properties to the latent heat storage material. With this in mind, crosslinked polymers which have been produced, for example, by copolymerization, and also mineral oil and, if necessary, further additives may be added to the paraffins.

In a further preferred embodiment, there is provision for the latent heat storage material 78 inside the drinks cooler 74 to be completely enclosed in a bag of film/foil which is impermeable to latent heat storage material, that side of the film/foil which is remote from the latent heat storage material bearing against the drink container and, in so doing, surrounding the container with latent heat storage material.

FIG. 20 shows a possible application of a latent heat body which contains a multiplicity of latent heat part-bodies 84. In detail, this application is an animal-feed container 26 with an outer casing 27 which corresponds to that of the animal-feed container 26 shown in FIG. 9. In contrast to FIG. 9, however, a multiplicity of latent heat part-bodies 84 are provided instead of a single-piece latent heat body 30, the volume filled by the latent heat part-bodies 84 amounting to more than ten times the volume of individual latent heat part-bodies 84. When further compared to FIG. 9, it can be seen from FIG. 20 that with a latent heat body which is formed from numerous smaller latent heat part-bodies, it is also possible to fill undercut casing shapes without problems. Moreover, in the animal-feed container shown in FIG. 20, the latent heat part-bodies can moreover preferably be compacted by mechanical action in the region adjoining the recess 28, so that a preferred heat or cold storage effect is achieved in that area.

Figure 21:
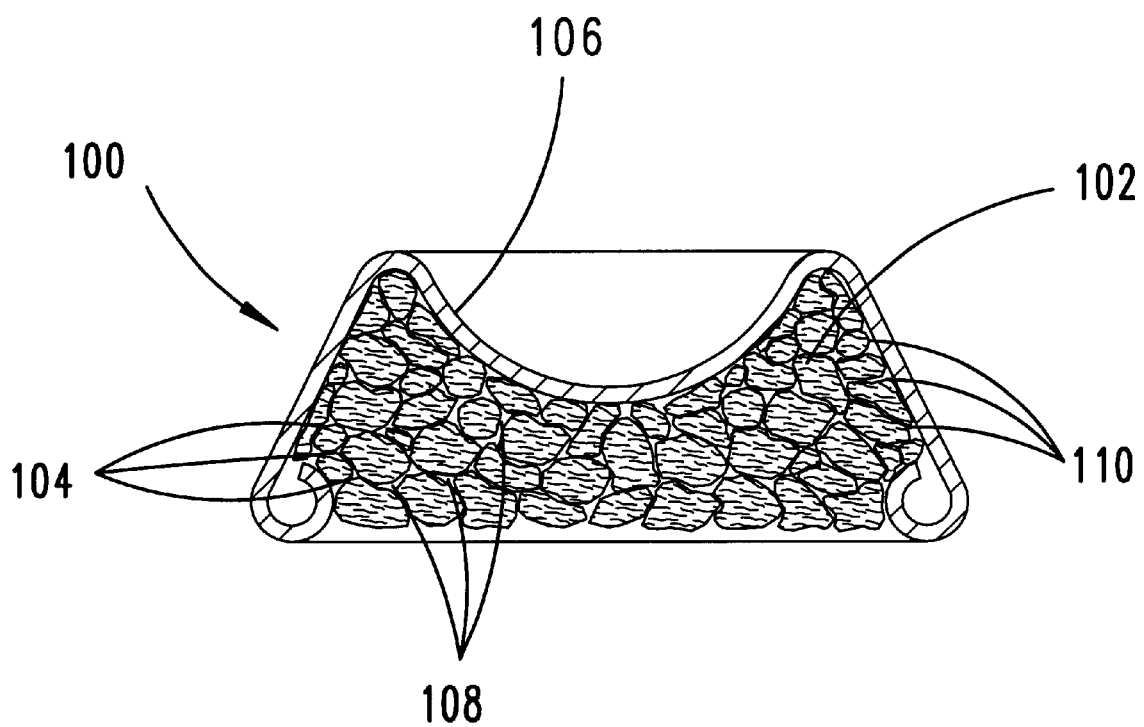
FIG. 21 shows latent heat body storage material within a container in accordance with the present invention.

FIG. 21 illustrates the carrier material 100 is assembled from individual carrier-material elements 102 which are inherently structurally strong or, when combined with the latent heat storage material, lead to the appropriate structural strength, for example by adhesive bonding as shown by the adhesive bonds 104 between the individual carrier-material elements 102. One means for forming an adhesive bond between the carrier material elements 102 is using glue. The carrier material 100 is positioned within a container 106. Capillary-like holding spaces 108 are formed between the individual carrier-material elements 102. The capillaries formed on the outer surface of the individual carrier-material elements may be closed to hold latent heat storage material therein by grinding or the like. Closure of the capillaries is indicated by the reference numeral 110.

All features disclosed are pertinent to the invention. The disclosure content of the associated/appended priority documents (copy of the prior application) is hereby incorporated as to its full content in the disclosure of the application, also for the purpose of including features of these documents in claims of the present application.

We claim:

1. Latent heat body (1) with paraffin-based latent heat storage material accommodated in a carrier material which has holding spaces, wherein the carrier material comprises fibers of an organic plastics material or natural material or of an inorganic material or of textile materials, and wherein the carrier material is assembled from individual carrier-material elements by adhesive bonding, capillary-like holding spaces for the latent heat storage material being formed at least between the carrier-material elements and wherein the latent heat storage material is provided with a thickening agent for providing increased viscosity to the heat storage material while in a molten state, wherein the latent heat storage material contains a proportion of mineral oil and polymers.

2. Latent heat body according to claim 1, wherein the mineral oil is highly-refined mineral oil.

3. Latent heat body according to claim 1, wherein the polymers are present in a proportion of less than 5% by mass of the latent heat storage material.

* * * * *